United States Patent [19]

Zirngibl et al.

[11] 4,210,657
[45] Jul. 1, 1980

[54] ARYL IMIDAZOLYL VINYL ETHERS AND PROCESSES FOR USING SAME

[75] Inventors: Ludwig Zirngibl, Zofingen; Johanna Fischer, Reiden; Kurt Thiele, Zofingen, all of Switzerland

[73] Assignee: Siegfried Aktiengesellschaft, Zofingen, Switzerland

[21] Appl. No.: 970,330

[22] Filed: Dec. 18, 1978

[30] Foreign Application Priority Data

Sep. 11, 1978 [DE] Fed. Rep. of Germany ....... 2839388

[51] Int. Cl.² .................. A61K 31/415; C07D 233/60
[52] U.S. Cl. ................. 424/273 R; 542/405; 542/411; 542/413; 542/426; 542/453; 542/458; 548/336; 548/337; 548/338; 548/341
[58] Field of Search ............... 542/405, 411, 453, 458, 542/413, 426; 548/336, 337, 338, 341; 424/273 R

[56] References Cited

U.S. PATENT DOCUMENTS

| | | | |
|---|---|---|---|
| 3,462,446 | 8/1969 | De Wald | 542/413 |
| 3,658,797 | 4/1972 | Ross et al. | 542/411 |
| 3,658,813 | 4/1972 | Godefroi et al. | 542/413 |
| 3,839,574 | 10/1974 | Godefroi et al. | 548/341 |
| 4,086,351 | 4/1978 | Balasubramanyan | 542/405 |

OTHER PUBLICATIONS

Hofmann Imidazoles and Its Derivatives, Part I, p. 127, N.Y., Interscience, 1953.
Godefroi et al., J. Med. Chem., 1969, vol. 12, pp. 784–791.

*Primary Examiner*—Natalie Trousof
*Attorney, Agent, or Firm*—Burns, Doane, Swecker & Mathis

[57] ABSTRACT

Aryl-imidazol-1-yl vinyl ethers and their acid addition salts are disclosed, wherein the imidazolyl vinyl ether has the formula:

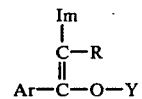

Ar in the formula represents a substituted or unsubstituted aryl or heterocyclic radical; R represents hydrogen or a $C_1$–$C_{12}$ alkyl or cycloalkyl (saturated or unsaturated) or Ar as above; Im represents a 1-H-imidazol-1-yl group (unsubstituted or substituted); and Y represents a saturated or unsaturated, acyclic or cyclic $C_1$–$C_{12}$ alkyl, or aryl or aralkyl, or an alkyl or alkylene residue directly bound to the ether oxygen and having a chain once or twice interrupted by —O—, —S—, —SO— or —SO$_2$— bridges. These compounds are effective wide spectrum fungicides and bactericides.

9 Claims, No Drawings

ARYL IMIDAZOLYL VINYL ETHERS AND PROCESSES FOR USING SAME

This invention concerns imidazolyl vinyl ethers of the general formula

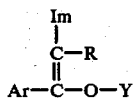
(I)

and their acid addition salts, wherein

Ar signifies a phenyl or naphthyl radical or a heterocyclic radical having one or two nuclei, wherein these radicals may be mono- or polysubstituted and the substituents may independently from each other be halogen, a lower alkyl or a cycloalkyl of 1 to 6 carbon atoms, trifluoromethyl, a lower alkoxy and a lower alkylthio with in each case from 1 to 6 carbon atoms in the alkyl portion, phenyl, benzyl, cyano, nitro or amino, R signifies an unbranched, branched or cyclic, saturated or unsaturated alkyl of 1 to 12, preferably 1 to 6 carbon atoms, which may contain one or more double- or triple carbon bonds, aryl or aralkyl having 1 to 6 carbon atoms in the alkyl portion, wherein "aryl" in each case may have the meaning previously given for the residue Ar including its substituents, or hydrogen when Y is not bonded to the vinyl ether oxygen via one of the groups —CH$_2$O—, —CH$_2$S—, —CH$_2$SO— or —CH$_2$SO$_2$—.

Im signifies a 1-H-imidazol-1-yl group which can be mono-, di- or trisubstituted with halogen, nitro, amino or an alkyl or alkoxy residue of 1 to 4 alkyl carbon atoms, and Y signifies an unbranched, branched or cyclic, saturated or unsaturated alkyl of 1 to 12, preferably 1 to 6 carbon atoms, which may be saturated or unsaturated and containing one or more double and/or triple carbon bonds, aryl or aralkyl having 1 to 6 carbon atoms in the alkyl portion, wherein "aryl" in each case may have the meaning previously given for the residue Ar including its substituents, and an alkyl residue directly bound to the ether oxygen or an alkylene group directly bound to the ether oxygen and which may be once or twice interrupted by —O—, —S—, —SO— or —SO$_2$— bridges.

The invention further concerns the use of these imidazolyl vinyl ethers and their pharmaceutically harmless acid addition salts as a fungicidal and/or bactericidal agent in medicinal compositions for human or veterinary medicine or in plant protection agents.

In the copending U.S. patent application Ser. No. 970,312 filed simultaneously herewith and corresponding to German OS 27 57 113, which is fully incorporated herein by reference, imidazolyl vinyl ethers are described having the general formula

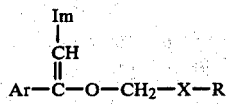
(II)

where in the general formula (II) the residues Ar, Im and R essentially have the same meaning as in general formula (I) and X represents —O—, —S—, —SO— or —SO$_2$—.

Imidazol-1-yl derivatives are easily obtainable fungicides and bactericides of low toxicity with a wide spectrum of activity. However, resistances and partial resistances are frequently observed when they are used. The imidazolyl vinyl ethers of the general formula (I) show in many cases a satisfactory activity where the imidazolyl vinyl ethers of the general formula (II) bring about resistance. The imidazolyl vinyl ethers of the general formula (I) supplement, widen and intensify the spectrum of activity heretofore made available by means of the imidazolyl vinyl ethers of general formula (II).

For the preparation of imidazolyl vinyl ethers of the general formula (I) the corresponding 1-arylacylimidazole having the general formula

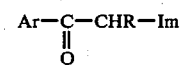
(III)

is reacted with a halide of the general formula

(IV)

in the presence of NaH with initial cooling with ice and subsequent mild heating and worked up in the usual manner. Hal in general formula (IV) signifies a halogen atom and Y has the meaning given above in connection with formula (I). The reaction is conducted with stirring in a solvent, preferably in hexamethylphosphoric acid triamide.

In a few cases the C-alkylation can not be totally prevented when using the above described manner of preparation. However, the ethanone derivatives of the general formula

(V)

which are thus obtained as byproducts only become apparent in the chromatographic column separation after the less polar substances of the general formula (I) have been eluted, and thus are readily separable from the desired products.

Besides the above named sodium hydride, which is preferably added as a dispersion in white mineral oil, alkali metals, alkaline earth metals as well as their hydrides and alcoholates, lithium organic compounds, sodium amide or mono- or di-N-substituted sodium amides can be used as condensation agents.

The invention is further described by means of the following examples.

EXAMPLE 1

1-(2,4-Dichlorophenyl)-1-(methoxymethoxy)-2-(imidazol-1-yl)propene.

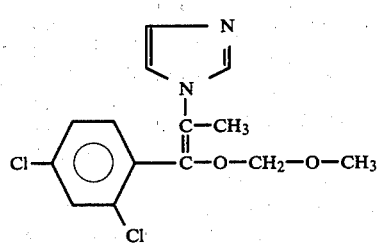

6.73 g (25 mmol) 2,4-dichloro-α-(imidazol-1-yl)propiophenone (J. med. Chem. 12, 790) are dissolved in 30 ml hexamethylphosphoric acid triamide and mixed with 0.63 g (26 mmol) of a 50% dispersion of NaH in highly refined white mineral oil in the course of 1.5 hours at 5° C. The mixture is heated one hour at 50° C., then cooled to 5° C. and 2.26 g (28 mmol) chlorodimethyl ether is added dropwise. In this the temperature of the reaction mixture is maintained at 5° to 10° C. by cooling. After addition of the chlorodimethyl ether one stirs for one hour at room temperature and five hours at 50° C. Subsequently the reaction mixture is poured into water. The separated oil is taken up in chloroform. After a separation of the organic phase the aqueous phase is extracted with ether. The extracts are separately dried, purified and completely stripped of solvent by evaporation. 5.27 g of an oily substance is obtained which is twice chromatographically separated on a silica gel column using chloroform as a carrier. 1.66 g of a pure end product is obtained in this manner as an oily substance.

The purity of the obtained substance is tested in an IR spectrum.

Elemental analysis for $C_{14}H_{14}Cl_2N_2O_2$ (mol. wt. 313.2):

|  | C (%) | H (%) | N (%) | Cl (%) |
| --- | --- | --- | --- | --- |
| Calculated: | 53.69 | 4.51 | 8.94 | 22.64 |
| Found: | 52.45 | 4.91 | 8.83 | 22.87 |

EXAMPLE 2

1-(2,4-Dichlorophenyl)-1-(4-chlorophenoxymethoxy)-2-(imidazol-1-yl)propene nitrate

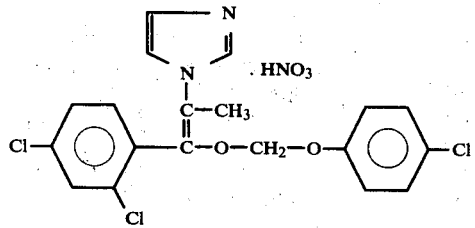

The process described in example 1 is repeated except that in place of chlorodimethyl ether the equivalent amount of chloromethyl-4-chlorophenyl ether is added. After recrystallization the pure crystalline nitrate shows a melting point of 115.5° to 118.5° C.

Elemental analysis for $C_{19}H_{15}Cl_3N_2O_2.HNO_3$ (mol. wt. 472.7):

|  | C (%) | H (%) | N (%) | O (%) |
| --- | --- | --- | --- | --- |
| Calculated: | 48.27 | 3.42 | 8.88 | 16.92 |
| Found: | 48.21 | 3.37 | 8.59 | 16.88 |

The $^1$H-NMR spectra give at 100 MHz in $d_6$-DMSO the following signal positions δ (ppm): 1.90 (s, 3H, —CH$_3$); 5.23 (s, 2H, —OCH$_2$O—); 6.84 (d, 2H, aromat. H (2') and (6')); 7.25 (d, 2H, aromat. H (3') and (5')); 7.63–7.82 (m, 5H, aromat. H and imidazolyl-4,5-H); 9.24 (s, 1H, imidazolyl-2H).

EXAMPLE 3

2-(2,4-Dichlorophenyl)-2-(ethoxy)-1-(imidazol-1-yl)ethylene nitrate

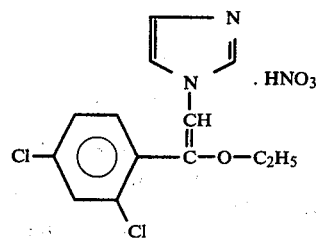

5.10 g (20 mmol) 1-(2,4-chlorophenacyl)imidazole (J. med. Chem. 12, 790) are dissolved in 25 ml hexamethylphosphoric acid triamide in a three-neck flask equipped with a reflux condenser, a dropping funnel and magnetic stirrer. To the solution is added 0.96 g (20 mmol) NaH in the form of a 50% NaH dispersion in highly refined, white mineral oil. It is stirred for two hours at room temperature and then one hour at 45° C. After cooling, 1.62 ml (20 mmol) ethyl iodide is added dropwise. The reaction proceeds strongly exothermally. A temperature of 10° to 15° C. is maintained in the reaction mixture during the addition of the ethyl iodide by cooling with ice. Subsequently one stirs twenty hours at room temperature. The reaction mixture is then poured into 300 ml water and shaken three times with ethyl acetate. The purified organic phases are dried with sodium sulfate and completely concentrated by evaporation. Thus 8.7 g of an oily substance is obtained which is chromatographically purified on a silica gel column using dichloromethane as a carrier. The purity of the fractions is checked in a thin layer chromatogram. The eluate fractions having the same pure thin layer chromatogram are combined, evaporated, taken up in ethyl acetate and precipitated with HNO$_3$. 1.9 g of a pure nitrate having a melting point of 131° to 134° C. is obtained.

Elemental analysis for $C_{13}H_{12}Cl_2N_2O.HNO_3$ (mol. wt. 356.2):

|  | C (%) | H (%) | N (%) |
| --- | --- | --- | --- |
| Calculated: | 45.10 | 3.78 | 12.14 |
| Found: | 45.30 | 3.74 | 12.00 |

In a $^1$H-NMR spectrum there are observed at 100 MHz in $d_6$-DMSO the following signal position in δ (ppm): 1.22 (t, 3H, —CH$_3$); 3.74 (q, 2H, —CH$_2$); 6.75 (s, 1H, C=CH—); 7.60 (s, 2H, imidazolyl-4,5-H); 7.78 (d, 2H, aromat. H (5), H (6)); 7.98 (s, 1H, aromat. H (3)); 9.38 (s, 1H, imidazolyl-2-H).

EXAMPLE 4

2-(2,4-Dichlorophenyl)-2-(2-(4-chlorophenoxy)-ethoxy))-1-(imidazol-1-yl)ethylene nitrate

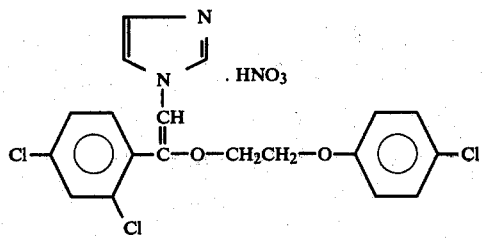

The process described in example 3 is repeated except that instead of ethyl iodide an equivalent amount of 4-chlorophenyl-2-iodoethyl ether is added. The nitrate which is precipitated in the form of white crystals has a melting point of 151° to 153° C.

EXAMPLE 5

2-(4-Chlorophenoxyethoxyethoxy)-2-(2,4-dichlorophenyl)-1-(imidazol-1-yl)ethylene nitrate

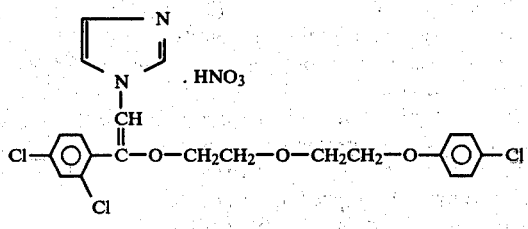

2,2'-Dichlorodiethyl ether and p-chlorophenol are converted to 4-chlorophenoxyethoxy-ethyl chloride in dilute aqueous sodium hydroxide and worked up in the usual manner. The obtained pure 4-chlorophenoxyethoxy-ethyl chloride has a boiling point of 110° to 113° C. at a pressure of 0.0013 mbar ($n_{20}^D$ 1.5315; $d_{20}^{20}$ 1.249).

In a manner analogous to the process described in example 3 20 mmol of the thus obtained 4-chlorophenoxyethoxyethyl chloride are reacted with the equivalent amount of 1-(2,4-dichlorophenacyl)imidazol.

The finally obtained purified nitrate has a melting point of 92° to 94° C. and shows no carbonyl band in the IR spectrum (in KBr).

EXAMPLE 6

2-(2,4-Dichlorophenyl)-2-(3-(4-chlorophenoxy)-propoxy)-1-(imidazol-1-yl)ethylene nitrate

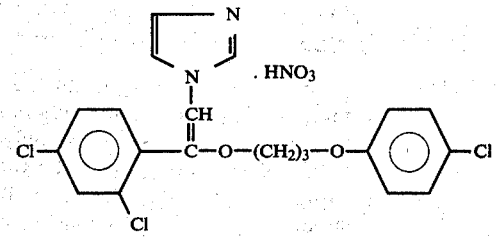

The nitrate prepared in a process analogous to the one described in detail in example 3 has a melting point of 116° to 117° C. and shows no carbonyl band in the IR spectrum (in KBr).

In a manner analogous to the procedure described in example 1 the following compounds are prepared:

1-(2,4-dichlorophenyl)-1-(n-butoxy)-2-(imidazol-1-yl)propene;
1-(2,4-dichlorophenyl)-1-(n-hexyloxy)-2-(imidazol-1-yl)propene; and
1-(2,4-dichlorophenyl)-1-(N,N-diethylaminoethoxy)-2-(imidazol-1-yl)propene.

EXAMPLE 7

2-(2,4-Dichlorophenyl)-2-(2-(4-chlorophenoxy)-ethoxy))-1-(imidazol-1-yl)ethylene nitrate

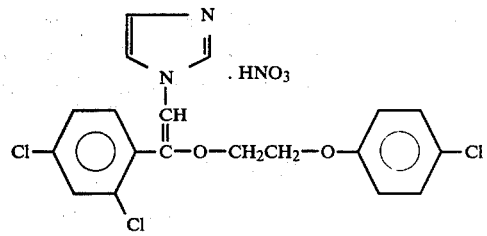

The compound which has previously been prepared according to example 4 is prepared according to a different process variation:

A three-neck flask fitted with a reflux condenser, a dropping funnel and a magnetic stirrer is charged with a solution of 16.41 g (63 mmol) 1-(2,4-dichlorophenacyl)-imidazole in 90 ml hexamethylphosphoric acid triamide. A total of 2.88 g (ca. 69 mmol) sodium hydride in the form of a 55 to 60 weight percent dispersion in highly refined, white mineral oil is added in two portions to the solution. It is stirred one hour at room temperature and then twenty minutes at 60° C. After cooling to room temperature 14.13 g (60 mmol) 2-(4-chlorophenoxy)ethylbromide is added dropwise, which was prepared from 1,2-dibromomethane (Bull. Soc. Chim. France 1957, 1014). The addition is carried out while stirring. The reaction mixture is allowed to stand 14 to 16 hours at room temperature and then once again heated one hour at 60° C. After the cooling the reaction mixture is poured into 1.6 l water and extracted with ethyl acetate. The purified extracts are dried with sodium sulfate. Subsequently the ethyl acetate solvent is removed under reduced pressure. One obtains 29.2 g of an oil as a residue, from which 9.2 g (19.5 mmol) of the product nitrate are precipitated upon addition of concentrated nitric acid and ether. After recrystallization from 50% aqueous alcohol a crystalline product is obtained having a melting point of 151° to 153° C. The IR spectrum of this compound no longer shows a carbonyl band.

Elemental analysis for $C_{19}H_{15}Cl_3N_2O_2 \cdot HNO_3$ (mol. wt. 472.2):

|  | C (%) | H (%) | N (%) |
| --- | --- | --- | --- |
| Calculated: | 48.27 | 3.41 | 8.89 |
| Found: | 48.57 | 3.35 | 9.35 |

EXAMPLE 8

2-(2,4-Dichlorophenyl)-2-(n-butoxyl)-1-(imidazol-1-yl)ethylene nitrate

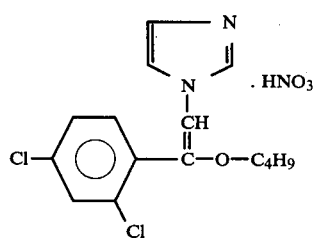

The compound is prepared in a manner analogous to the process described in example 7. After recrystallization from aqueous alcohol the white crystalline product melts at 153° to 154° C.

EXAMPLE 9

2-(2,4-Dichlorophenyl)-2-(n-hexyloxy)-1-(imidazol-1-yl)-ethylene nitrate

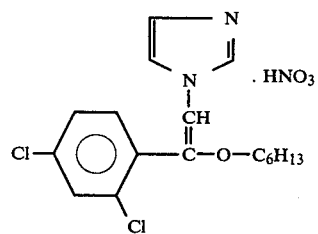

The compound is prepared in a manner analogous to that described in example 7. After recrystallization the purified nitrate shows a melting point of 113° to 115° C.

EXAMPLE 10

2-(2,4-Dichlorophenyl)-2-(2-diethylaminoethyloxy)-1-(imidazol-1-yl)ethylene dinitrate

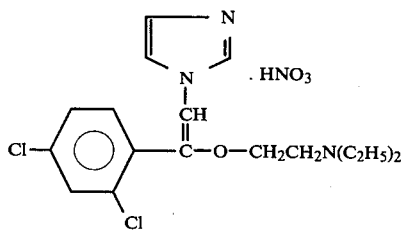

The compound is prepared in a manner analogous to that described in example 7. After acidifying with concentrated nitric acid, a dinitrate precipitates out in crystalline form, which is in contrast to the mononitrate formed in the case of the other imidazolyl vinyl ethers. After recrystallization the dinitrate has a melting point of 117° to 118.5° C.

EXAMPLE 11

2-(2,4-Dichlorophenyl)-2-(4-chlorophenoxyethoxy)-1-(imidazol-1-yl)-propene nitrate

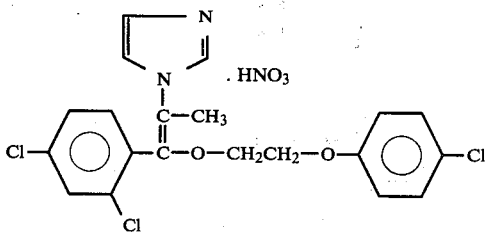

The compound is prepared in a manner analogous to that described in example 1, with subsequent precipitation by means of concentrated nitric acid and crystallization from aqueous alcohol. The resulting crystalline product nitrate has a melting point of 115° to 123° C.

TESTS

The compounds prepared according to examples 1 to 11 are evaluated for their batericidal and fungicidal activity. For comparison, the commercially available, well-known fungicide α-(2,4-dichlorophenyl)-β-imidazol-1-yl-ethyl-(4-chlorophenyl)-methylether nitrate, designated in Table 1 as "A", is evaluated under identical conditions.

For determination of the minimum blocking concentration (MIC), the gradient plate method with gradients from zero to 100 μg/ml is resorted to. The compounds to be examined are used as solutions in 10% dimethylformamide. Reading of the results takes place three days after starting the test. The resulting data are summarized in Table 1. The bacteria *Staphylococcus aureus haemolyticus* (St) and *Streptococcus faecalis* (Str) and the fungi *Candida albicans* (Ca), *Trichophyton mentagrophytes* (Tri) and *Aspergillus niger* (Asp) serve as test organisms. The cases in which resistances or partial resistances are observed are designated in Table 1 with an "r".

Table 1

| Example No. | MTC (μg/ml) Bacteria | | Fungi | | |
|---|---|---|---|---|---|
| | St | Str | Ca | Tri | Asp |
| 1 | 60 | 60 | <10 | <10 | <10 |
| 2 | <10 | <10 | r | <10 | <10 |
| 3 | 25 | 15 | <10 | <10 | <10 |
| 4 & 7 | <10 | r | r | <10 | <10 |
| 5 | 10 | 60r | r | <10 | 50r |
| 6 | 10 | 40r | — | <10 | 20r |
| 8 | <10 | <10 | <10 | <10 | <10 |
| 9 | <10 | <10 | r | <10 | <10 |
| 11 | <10 | <10 | r | <10 | <10 |
| A | <10 | — | r | <10 | <10 |

Table 1 shows the compounds of examples 1, 3 and 8 to be particularly desirable fungicides in that among all the compounds tested these three were the only ones that produced no noticeable resistance in the *Candida albicans* test organisms. However, Table 1 further shows that the compounds of all the examples 1–11 were also in all cases as good as the prior art compound A in controlling the *Trichophyton mentagrophytes* organism.

All the tested compounds that are illustrative of the invention also have shown themselves to be good in terms of controlling the Staphylccoccus bacteria.

The active compounds may be applied to infected substrates in an otherwise conventional manner in the form of dusts when diluted with solid carriers such as clays, or in the form of aqueous dispersions or solutions. They may also be included in an otherwise customary manner in soaps or in synthetic detergent compositions and used for washing the skin of patients, or walls or floors in infected areas, or hospital laundry, or the like.

The invention is particularly pointed out and claimed in the appended claims.

We claim:

1. An imidazolyl vinyl ether of the formula

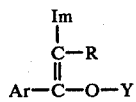
(I)

or an acid addition salt thereof acceptable for bactericidal or fungicidal use, wherein Ar signifies phenyl or naphthyl unsubstituted or mono- or polysubstituted with substituents that are independently selected from the group consisting of halogeno, alkyl and cycloalkyl of up to 6 carbon atoms each, trifluoromethyl, alkoxy and alkylthio of from 1 to 6 carbon atoms in the alkyl portion of each, phenyl, benzyl, cyano, nitro and amino, Im signifies unsubstituted 1-H-imidazol-1-yl or substituted 1-H-imidazol-1-yl which has 1 to 3 substituents independently selected from the group consisting of halogeno, alkyl and alkoxy of 1 to 4 carbon atoms, and not more than one nitro group, Y signifies (a) unbranched or branched aliphatic or cycloaliphatic hydrocarbyl of up to 12 carbon atoms which either is saturated or is unsaturated and contains one or more double and/or triple bonds, or (b) Ar as defined above, or (c) -Z-Ar wherein Ar is as defined above and Z is alkylene or alkylene having its carbon chain once or twice interrupted by a linkage selected from the group consisting or oxy, thio, sulfinyl or sulfonyl or (d) an aliphatic hydrocarbyl as defined in (a) above wherein the carbon chain linked to the ether oxygen is once or twice interrupted by a linkage selected from the group consisting of oxy, thio, sulfinyl and sulfonyl, and R signifies (i) unbranched or branched aliphatic or cycloaliphatic hydrocarbyl of up to 12 carbon atoms which is either saturated or contains one or more double and/or triple bonds, (ii) Ar as defined above, or (iii) hydrogen but only if Y is not —CH$_2$—X—R'' wherein X represents oxy, thio, sulfinyl or sulfonyl and R'' is (a) unbranched or branched aliphatic or cycloaliphatic hydrocarbyl of up to 12 carbon atoms which is either saturated or contains one or more double and/or triple bonds or (b) Ar as defined above.

2. An imidazolyl vinyl ether according to claim 1 having the formula

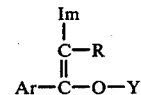

or an acid addition salt thereof acceptable for bactericidal or fungicidal use, wherein Ar is dichlorophenyl, R is either hydrogen or methyl, and Y is either alkyl of 2 to 4 carbon atoms or alkoxyalkyl of 2 to 4 carbon atoms.

3. An imidazoyl vinyl ether selected from the group consisting of 2-(2,4-dichlorophenyl)-2-ethoxy-1-(imidazol-1-yl)ethylene, 2-(2,4-dichlorophenyl)-2-(n-butoxy)-1-(imidazol-1-yl)ethylene, 1-(2,4-dichlorophenyl)-1-(n-butoxy)-2-(imidazol-1-yl)propene, and 1-(2,4-dichlorophenyl)-1-(methoxymethoxy)-2-(imidazol-1-yl)propene, and nitrate salts thereof.

4. A compound selected from the group consisting of 2-(2,4-dichlorophenyl)-2-(2-(4-chlorophenoxy)-ethoxy)-1-(imidazol-1-yl) ethylene nitrate and 3-(2,4-dichlorophenyl)-3-(2-(4-chlorophenoxy)ethoxy)-2-(imidazol-1-yl)-2-propene nitrate.

5. 2-(2,4-Dichlorophenyl)-2-(2-4-chlorophenoxy)ethoxy)-1-(imidazol-1-yl)ethylene nitrate.

6. A fungicidal composition comprising an effective amount of at least one of the compounds of claim 1 in admixture with an inert carrier.

7. A fungicidal composition comprising an effective amount of at least one nitrate salt of one of the ethers of claim 4.

8. A process for controlling fungi or bacteria which comprises applying thereto an effective amount of a compound of claim 1.

9. A process for controlling fungi selected from the group consisting of *Candida albicans, Trichophyton mentagrophytes* or *Aspergillus niger* which comprises applying to said fungi a fungicidally effective amount of at least one compound of claim 4.

* * * * *